US009701427B2

(12) United States Patent
Algrain et al.

(10) Patent No.: US 9,701,427 B2
(45) Date of Patent: Jul. 11, 2017

(54) DEVICE FOR INTERFACING A FLUID INJECTION INSTRUMENT WITH A PUNCTURABLE FLASK AND METHOD FOR USE THEREOF

(71) Applicant: Vygon, Ecouen (FR)

(72) Inventors: Isabelle Algrain, Puiseux-en-France (FR); Jean-Luc Carrez, Ecouen (FR); Jean-Louis Coussegal, Beauchamp (FR); Pierrick Guyomarc'h, Ermont (FR); Marie-Hélène Pech, Paris (FR); Patrick Lestoquoy, Attiches (FR)

(73) Assignee: Vygon (FR)

( * ) Notice: Subject to any disclaimer, the term of this patent is extended or adjusted under 35 U.S.C. 154(b) by 157 days.

(21) Appl. No.: 14/358,472

(22) PCT Filed: Nov. 15, 2012

(86) PCT No.: PCT/EP2012/072743

§ 371 (c)(1),
(2) Date: May 15, 2014

(87) PCT Pub. No.: WO2013/072421

PCT Pub. Date: May 23, 2013

(65) Prior Publication Data

US 2014/0283948 A1 Sep. 25, 2014

(30) Foreign Application Priority Data

Nov. 15, 2011 (FR) ...................................... 11 60397

(51) Int. Cl.
*A61B 19/00* (2006.01)
*B65B 3/00* (2006.01)
*A61J 1/20* (2006.01)

(52) U.S. Cl.
CPC ............. *B65B 3/003* (2013.01); *A61J 1/2096* (2013.01); *A61J 1/201* (2015.05); *A61J 1/2037* (2015.05);

(Continued)

(58) Field of Classification Search
CPC ........ A61J 1/2096; A61J 1/201; A61J 1/2037; A61J 1/2068; A61J 1/2075; A61J 1/1406; A61M 2039/267

(Continued)

(56) References Cited

U.S. PATENT DOCUMENTS

| | | | | |
|---|---|---|---|---|
| 4,564,054 | A * | 1/1986 | Gustavsson | A61J 1/2096 141/329 |
| 5,527,306 | A | 6/1996 | Haining | |
| 2007/0244460 | A1 | 10/2007 | Fangrow | |
| 2008/0142388 | A1 | 6/2008 | Whitley et al. | |

(Continued)

FOREIGN PATENT DOCUMENTS

| | | | |
|---|---|---|---|
| FR | 1160164 | A | 7/1958 |
| FR | 2928539 | A1 | 9/2009 |

(Continued)

OTHER PUBLICATIONS

International Search Report for Application No. PCT/EP2012/072743 dated Dec. 19, 2012.

(Continued)

*Primary Examiner* — Leslie Deak

(74) *Attorney, Agent, or Firm* — Lerner, David, Littenberg, Krumholz & Mentlik, LLP

(57) ABSTRACT

The invention concerns an interfacing device (1) intended to connect a fluid injection instrument and a puncturable flask (2), comprising:

Figure 1A:
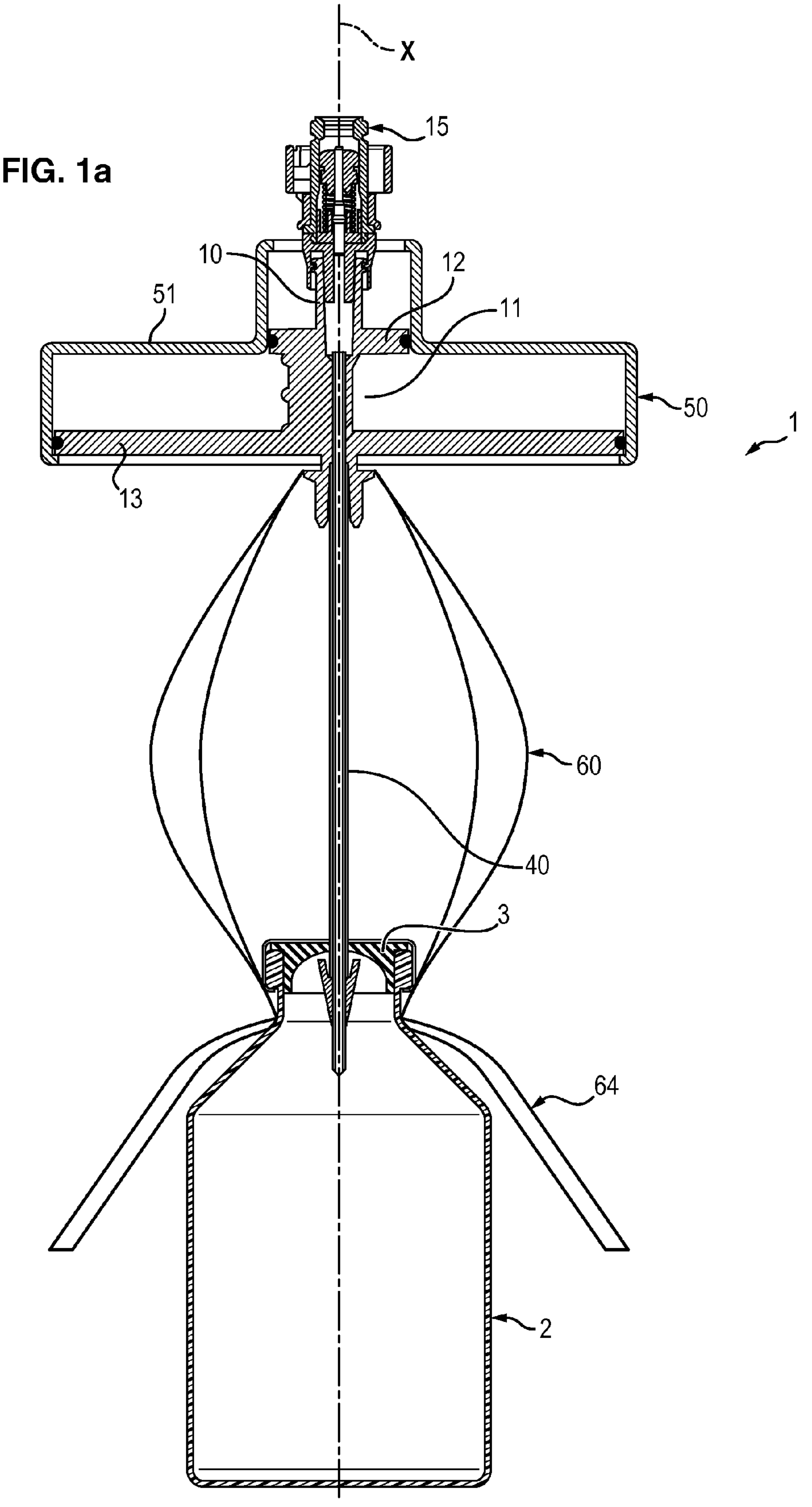

a base (10) suitable for connecting the interfacing device (1) to the fluid injection instrument, an attachment means for attaching (20) the base (10) to the puncturable flask (2), arranged at a distal end (1*a*) of the interfacing device (1), characterized in that the attachment means for attaching (20) has a divergent proximal end (21) forming a shoulder and a (Continued)

convergent distal end (22) suitable for facilitating the penetration of the attachment means for attaching (20) into the puncturable flask (2).

13 Claims, 9 Drawing Sheets

(52) U.S. Cl.
CPC ............ *A61J 1/2055* (2015.05); *A61J 1/2072* (2015.05); *A61J 2200/10* (2013.01)

(58) Field of Classification Search
USPC .......................................................... 604/415
See application file for complete search history.

(56) References Cited

U.S. PATENT DOCUMENTS

2010/0147402 A1* 6/2010 Tornqvist .............. F16K 15/147
137/513

FOREIGN PATENT DOCUMENTS

| | | | |
|---|---|---|---|
| FR | 2951638 | A1 | 4/2011 |
| WO | 2006138184 | A2 | 12/2006 |
| WO | 2009112535 | A1 | 9/2009 |

OTHER PUBLICATIONS

French Preliminary Search Report for Application No. FR 1160397 dated Jun. 15, 2012.

* cited by examiner

DEVICE FOR INTERFACING A FLUID INJECTION INSTRUMENT WITH A PUNCTURABLE FLASK AND METHOD FOR USE THEREOF

CROSS-REFERENCE TO RELATED APPLICATION

The present application is a national phase entry under 35 U.S.C. §371 of International Application No. PCT/EP2012/072743, filed Nov. 15, 2012, which claims the benefit of priority to French Patent Application No. 1160397, filed Nov. 15, 2011, the disclosure of which is incorporated herein by reference.

The invention relates to an interfacing device intended to connect a fluid injection instrument such as a syringe and a puncturable flask (called Vial) containing a drug for the purposes of preparing fluids intended to be perfused in a patient.

In oncology, for the treatment of cancerous tumours, it is necessary to perfuse fluids that can be very aggressive. The preparation of these fluids, which have the form of a solute, can be dangerous for the care-giving personnel in that they are very aggressive and can be the source of accidents with toxic or allergic effects. In many cases, the drug that must be administered has the form of a powder in a vacuum flask, which is sealed by a plus with an elastomeric membrane.

In order to mix this drug contained in such a vacuum flask with a fluid intended to be perfused, in a first step the drug in the form of a powder must be diluted in this liquid using a syringe generally provided with a needle. The fluid to be perfused can for example be physiological serum (distilled water+NaCl).

The plug with an elastomeric membrane of the flask is then passed through with the needle, which has for effect to cause air to suddenly enter into the flask that was in a vacuum. This air mixes with the drug in the form of a powder and can exit partially carrying pure drug, which is dangerous for the care-giving personnel in charge of the preparation. Once the needle of the syringe is put into place through the plug with an elastomeric membrane, the care-giving personnel in charge of the preparation pushes using the syringe the fluid to be perfused into the flask, which causes to exit, here again, the air initially enclosed in the flask loaded where applicable with particles of drugs that are not yet diluted.

The flask is then shaken and the mixture is drawn through the plug with an elastomeric membrane using the syringe. In practice, the liquid mixture to be perfused plus the diluted drug is injected and drawn several times in and out of the flask with the syringe, in order to thoroughly mix the drug in the liquid. However, such a mixture causes air to enter into and exit from the flask, which entails risks of pollution on the one hand for the care-giving personnel in charge of the preparation, and on the other hand for the mixture prepared.

Finally, the needle is removed from the flask. It must then be disconnected from the syringe without pricking oneself and preventing any direct contact of the mixture created as such with the care-giving personnel in charge of the preparation. The filled syringe is then connected near the patient to an infusion bag connected to the latter or connected directly to the patient himself.

During this manipulation, the main causes of accident are linked to the problems with the tightness to liquids and to gases from the inside of the Vial to the outside environment, with dissemination of dangerous products, which can come into contact with the skin, the eyes and the respiratory system of the preparing and care-giving personnel, but also to problems of tightness from the outside environment to the interior of the Vial which risk contaminating the preparation, or problems of vertical stability of the interfacing device. It may therefore be necessary for the preparing personnel to work in confined areas, under a hood or in enclosures, and with thick gloves.

Such interfacing devices are already known. For example, document FR 2 928 539 proposes an interfacing device comprising means for circulating air, intended to allow for the entering and exiting of air from the puncturable flask, provided with means for filtering air suited to retain the particles of pure drug not yet diluted during the exiting of air from the flask, as well as impurities contained in the ambient air penetrating into the flask during the entry of air into the flask. The device therefore makes it possible to secure the manipulation and the preparation of the mixture.

However, the use of this device results in several entries and exits of in the Vial which poses further problems in terms of safety. Indeed, the means of filtering, which is generally in the form of an exhaust filter, is highly sensitive to liquids and its filtering does not appear to be sufficiently efficient for the users.

Moreover, the device is relatively complex to carry out and comprises a large number of parts.

Document FR 2 951 638 therefore proposes an interfacing device comprising a base whereon is fixed a reservoir of air via means for circulating air, wherein the reservoir of air comprises a rigid shell associated with a flexible membrane, defining a compartment isolated from the exterior. This improved air circulation system then replaces the filter and allows for a circulation of air in the Vial, while still keeping the Vial isolated from the exterior and therefore from the risks of contamination by outside elements.

Such an interfacing device has good functionalities and makes it possible to effectively limit the risks of contamination. However, its design is very expensive and complex.

An objective of the invention is therefore to propose an interfacing device that is in addition of low cost and less complex to carry out, while still reducing the risks of contamination, whether of the contents of the Vial by outside elements or of the preparing or care-giving personnel by the contents of the Vial.

Optionally, the invention also has for objective to propose an interfacing device that is stable in all the positions and during the manipulations when it is fixed on the Vial.

For this, according to a first aspect, the invention proposes an interfacing device intended to connect a fluid injection instrument and a puncturable flask, comprising:

a base suitable for connecting the interfacing device to the fluid injection instrument, an attachment means for attaching the base onto the puncturable flask, arranged at a distal end of the interfacing device, wherein the attachment means for attaching has a divergent proximal end forming a shoulder and a convergent distal end suitable for facilitating a penetration of the attachment means for attaching into the puncturable flask, and the attachment means for attaching comprises at least one indentation in a zone adjacent to its proximal end, suited to place in fluidic communication the puncturable flask with an external space of the interfacing device.

Alternatively, an interfacing device in accordance with the invention has the following characteristics, taken independently or in any combination that can be considered by those skilled in the art in light of their general knowledge:

the attachment means for attaching comprises a generally tapered-shape body;

the proximal portion of the attachment means for attaching comprises at least one lug extending in the direction of the base from the body of the attachment means for attaching;

the proximal portion of the attachment means for attaching comprises two diametrically-opposed lugs extending in the direction of the base from the body of the attachment means for attaching;

the base and the distal end of the interfacing device include respectively a first and a second orifice in fluidic communication;

the device further comprises a means for puncturing the puncturable flask;

the means for puncturing is a needle of which the distal end is in the form of a tip;

the distal end of the needle is bevelled;

the attachment means for attaching is fixed on a distal end of the means for puncturing;

the attachment means for attaching is over-moulded in a zone adjacent to the distal end of the means for puncturing;

the device further comprises a cannula threaded onto the means for puncturing between the base and the attachment means for attaching;

an inner diameter of the cannula is greater than an outside diameter of the means for puncturing in such a way as to form an annular channel between the cannula and the needle;

the indentation is suited to place in fluidic communication the annular channel with the space external to the interfacing device;

the device further comprises a variable-volume reservoir fixed in a sealed manner onto the base and in fluidic communication with the annular channel;

a maximum volume of the variable-volume reservoir is greater than or equal to an internal volume of the puncturable flask;

the variable-volume reservoir is an elastomeric or thermoplastic ball;

the device has a main extension axis, and the ball extends transversally in relation to said main extension axis;

the ball is inclined in relation to the main extension axis, in such a way as to bring closer a centre of gravity to the ball of said main extension axis;

the device has a main extension axis, and the variable-volume reservoir extends transversally to said main extension axis of the interfacing device entirely or partially around the base;

the variable-volume reservoir comprises a support and a casing assembled together in a sealed manner and mobile in translation in relation to one another;

the casing is assembled with the support by means of a seal;

the support is formed from a proximal plate and from a distal plate substantially parallel and integral in translation, and the casing and the support are able to be displaced in relation to one another in a direction perpendicular to said plates;

the casing comprises a proximal portion, of cylindrical shape complementary with the shape of the proximal plate, and a distal portion, of cylindrical shape complementary with the distal plate, and the proximal portion and the distal portion are in sealed contact with the proximal plate and the distal plate respectively;

the device has a main extension axis and the proximal and distal plates are of cylindrical revolution and extend transversally to said main extension axis;

the variable-volume reservoir contains a sterile gas;

the cannula is fixed in relation to the means for puncturing;

the cannula is abutted against the attachment means for attaching;

the cannula is fixed on the attachment means for attaching;

the device further comprises a protective member fixed on the base and covering entirely or partially the attachment means for attaching;

the protective member is an envelope extending between a proximal end and a distal end diametrically opposite, the proximal end being suited to be fixed onto the base in such a way that the envelope covers at least partially a distal portion of the interfacing device in order to limit the risks of contamination;

the proximal end is suited to be fixed onto the base while the distal end is suited to be fixed onto the puncturable flask;

the proximal end is fixed by welding, gluing, snap-fitting or press-fitting onto the base;

the protective member further comprises at least one means for grasping extending from its distal end;

the distal end is a circular or elliptical ring; and the distal end of the protective member is an elliptical ring and the means for grasping comprises two grasping strips, arranged facing parallel to a large axis of the elliptical ring.

According to a second aspect, the invention proposes an interfacing device intended to connect a fluid injection instrument and a puncturable flask, comprising:

a base suitable for connecting the interfacing device to the fluid injection instrument, a means for puncturing the puncturable flask, extending from the base in the direction of a distal end of the device; and a variable-volume reservoir, fixed in a sealed manner onto the interfacing device, wherein the variable-volume reservoir is in fluidic communication with zone adjacent to a distal end of the means for puncturing in such a way that the interfacing device forms with the puncturable flask a closed system when the interfacing device is connected to said puncturable flask.

Alternatively, an interfacing device in accordance with the invention has the following characteristics, taken independently or in any combination that can be considered by those skilled in the art in light of their general knowledge:

the reservoir is fixed on the base, and the base and the adjacent zone of the distal end of the means for puncturing include respectively a first and a second orifice in fluidic communication;

the device further comprises an attachment means for attaching the base onto the puncturable flask, arranged at the distal end of the means for puncturing;

the attachment means for attaching has a divergent proximal end forming a shoulder and a convergent distal end suitable for facilitating a penetration of the attachment means for attaching into the puncturable flask;

the attachment means for attaching comprises a generally tapered-shape body and at least one lug extending in the direction of the base from the body of the attachment means for attaching;

the attachment means for attaching is fixed by means for puncturing in the zone adjacent to the distal end of the means for puncturing;

the attachment means for attaching is over-moulded onto the means for puncturing in the zone adjacent to the distal end of said means for puncturing;

the device further comprises a cannula threaded onto the means for puncturing between the base and the attachment means for attaching;

the means for puncturing is a needle of which the distal end is in the form of a tip;

an inner diameter of the cannula is greater than an outside diameter of the needle in such a way as to form an annular channel between the cannula and the needle, said channel being in fluidic communication on the one hand with the variable-volume reservoir and on the other hand with the zone adjacent to the distal end of the means for puncturing;

the attachment means for attaching comprises at least one indentation on its proximal end that opens into the annular channel, in such a way that the annular channel is in fluidic communication with a space external to the interfacing device;

a maximum volume of the variable-volume reservoir is greater than or equal to an internal volume of the puncturable flask;

the variable-volume reservoir is an elastomeric or thermoplastic ball;

the device has a main extension axis, and the ball extends transversally in relation to said main extension axis;

the ball is inclined in relation to the main extension axis, in such a way as to bring closer a centre of gravity to the ball of said main extension axis;

the device has a main extension axis, and the variable-volume reservoir extends transversally to said main extension axis of the interfacing device entirely or partially around the base;

the variable-volume reservoir comprises a support and a casing assembled together in a sealed manner and mobile in translation in relation to one another;

the casing is assembled with the support by means of a seal;

the support is formed from a proximal plate and from a distal plate substantially parallel and integral in translation, and the casing and the support are able to be displaced in relation to one another in a direction perpendicular to said plates;

the casing comprises a proximal portion, of a cylindrical shape complementary with the shape of the proximal plate, and a distal portion, of cylindrical shape complementary with the distal plate, and the proximal portion and the distal portion are in sealed contact with the proximal plate and the distal plate respectively;

the device has a main extension axis and the proximal and distal plates are of cylindrical revolution and extend transversally to said main extension axis; and the device further comprises a protective member fixed on the base and covering at least partially a distal portion of the interfacing device in order to limit the risks of contamination.

According to a third aspect, the invention proposes a protective member for an interfacing device intended to connect a fluid injection instrument and a puncturable flask, the interfacing device comprising:

a base suitable for connecting the interfacing device to the fluid injection instrument, an attachment means for attaching the base onto the puncturable flask, arranged at a distal end of the interfacing device, the protective member being characterised in that it comprises an envelope extending between a proximal ring and a distal ring diametrically opposite, the proximal ring being suited to be fixed on the base in such a way that the envelope covers entirely or partially a distal portion of the interfacing device in order to limit the risks of contamination.

Alternatively, a protective member in accordance with the invention can have the following characteristics, taken independently or in combination:

the proximal ring and the distal ring are of circular or elliptical shape;

the protective member further comprises means for grasping extending from the distal ring;

the means for grasping are two grasping strips;

the distal ring is of elliptical shape and the grasping strips extend on either side of a large axis of the distal ring;

at least one of the grasping strips has an adhesive surface;

the adhesive surface is provided with a peelable protective film.

According to a last aspect, the invention proposes an interfacing device intended to connect a fluid injection instrument and a puncturable flask, comprising:

a base suitable for connecting the interfacing device to the fluid injection instrument, an attachment means for attaching the base onto the puncturable flask, arranged at a distal end of the interfacing device, and comprising a protective member fixed on the base in such a way as to cover at least partially a distal portion of the interfacing device in order to limit the risks of contamination.

Alternatively, the proximal ring can be suited to be fixed by gluing, welding, locking or by means of an elastic sleeve on the base.

Figure 1B:
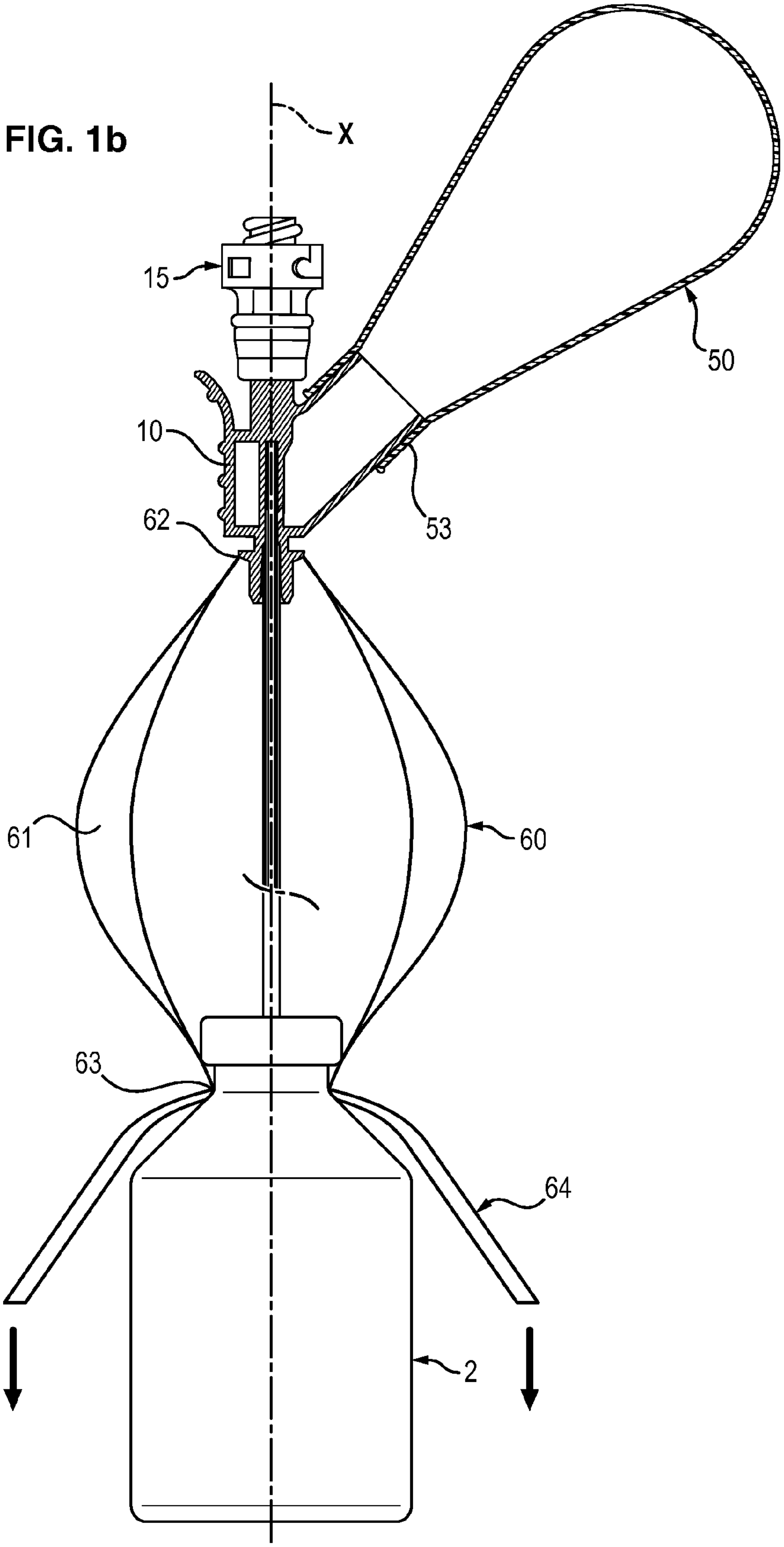
Figure 2:
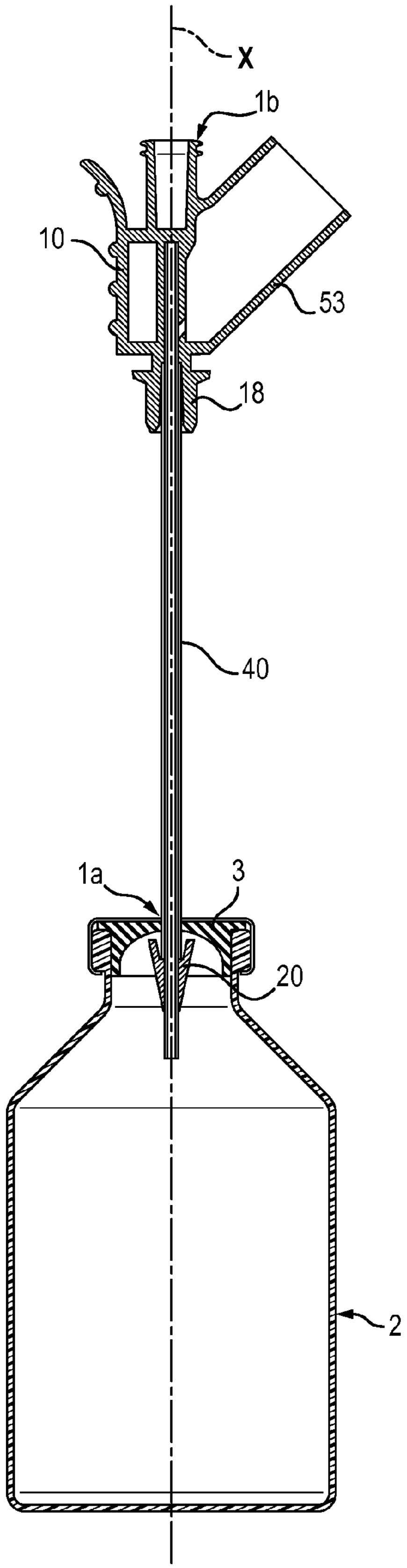
Figure 3A:
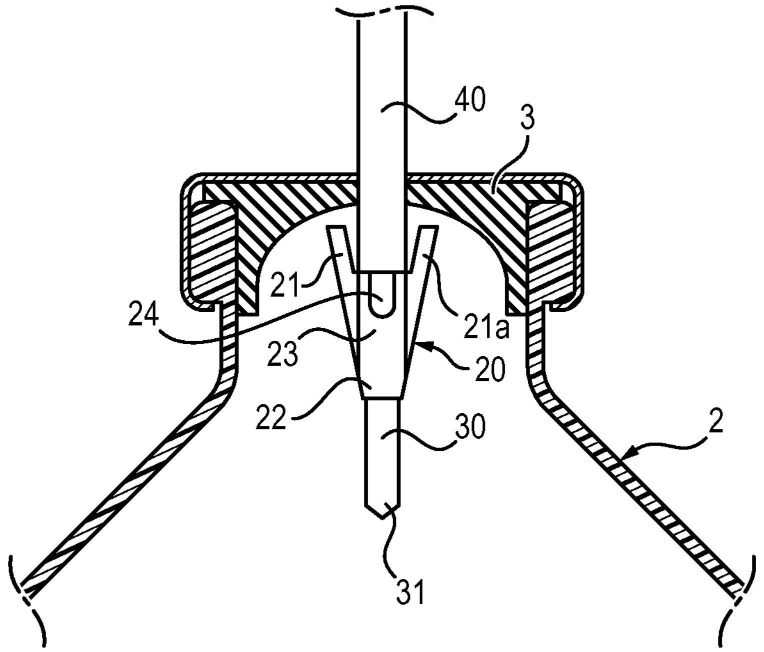
Figure 3B:
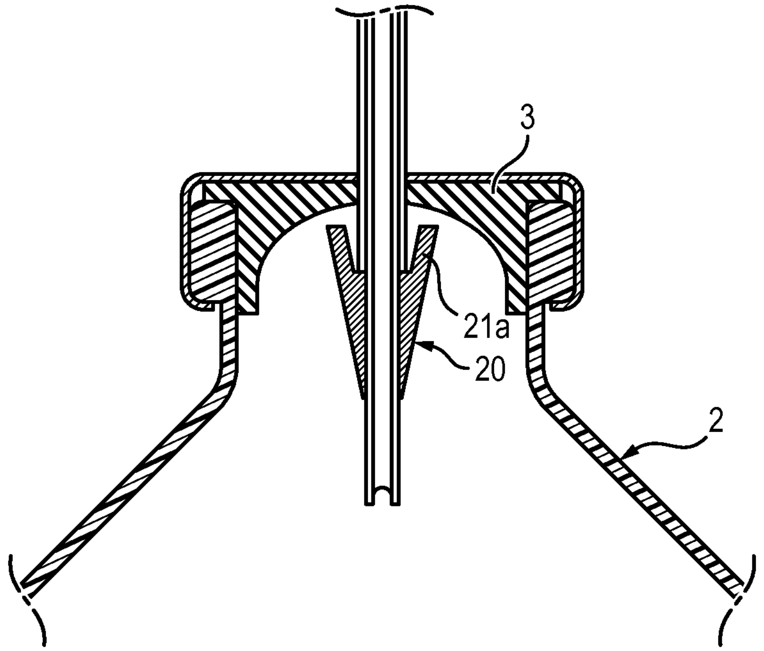

Other characteristics, purposes and advantages of this invention shall appear more clearly when reading the following detailed description, made in reference to the annexed figures provided in a non-limited manner and wherein:

FIG. 1*a* shows a cross-section view of a first embodiment of an interfacing device in accordance with the invention fixed on a Vial;

FIG. 1*b* shows a cross-section view of a second embodiment of an interfacing device in accordance with the invention fixed on a Vial;

FIG. 2 shows a cross-section view of a third embodiment of an interfacing device in accordance with the invention fixed on a Vial;

FIG. 3*a* is a close-up partial cross-section of a Vial passed through by the attachment means for attaching of FIGS. 1*a*, 1*b* and 2;

FIG. 3*b* is a cross-section view of FIG. 3*a;*

Figure 4:
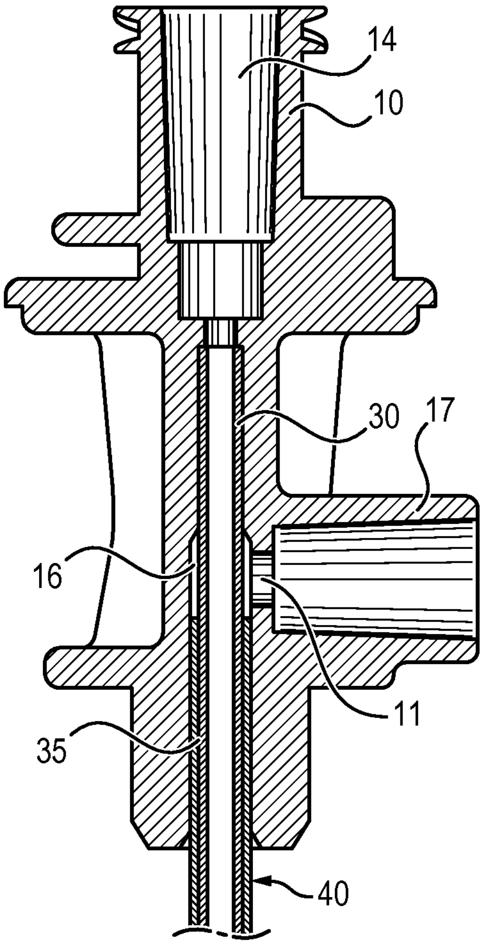
Figure 5A:
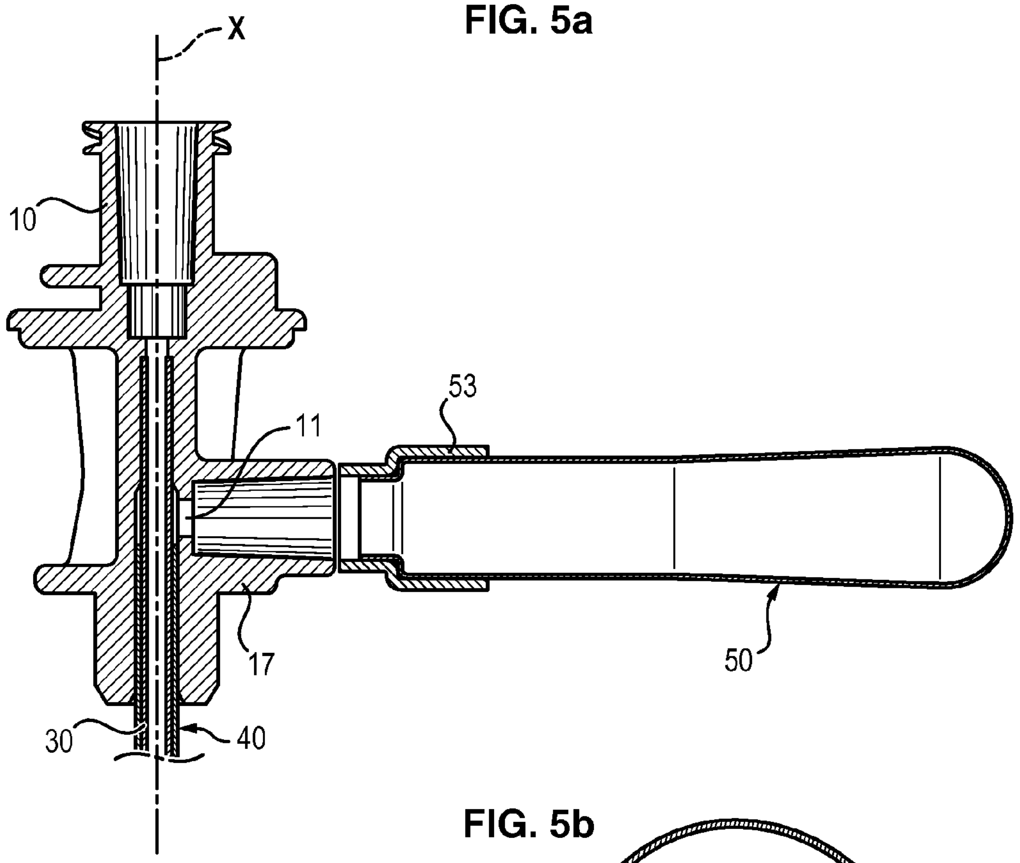
Figure 5B:
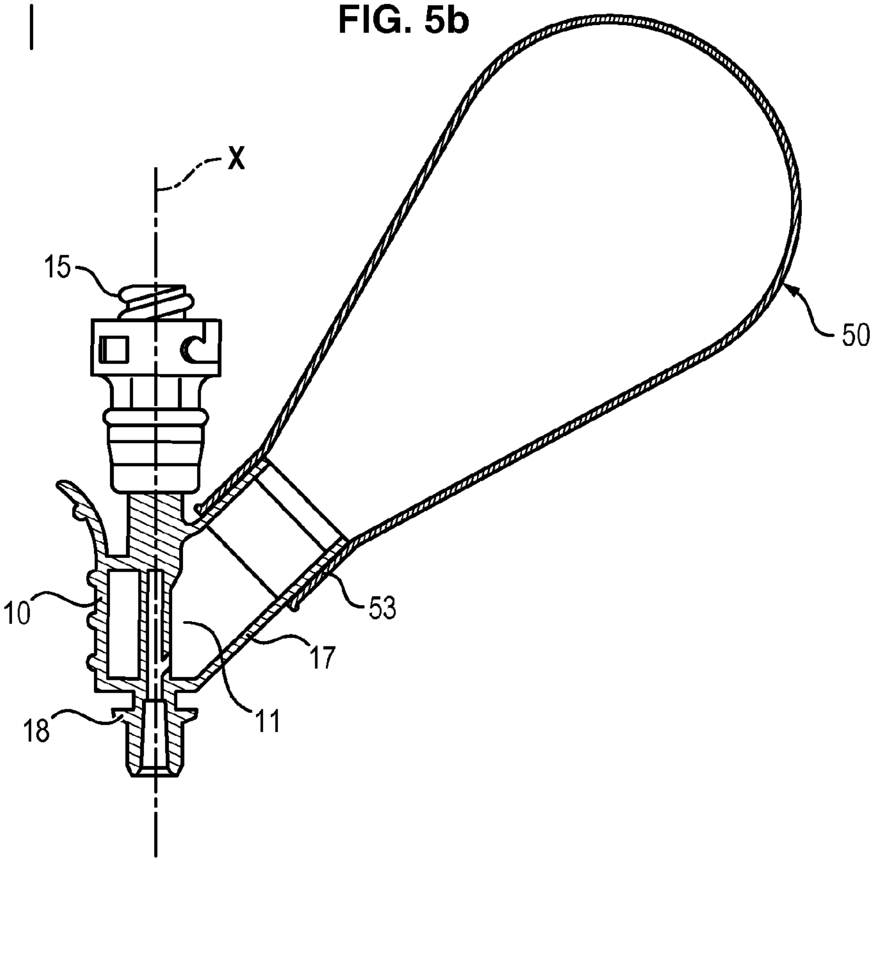
Figure 6A:
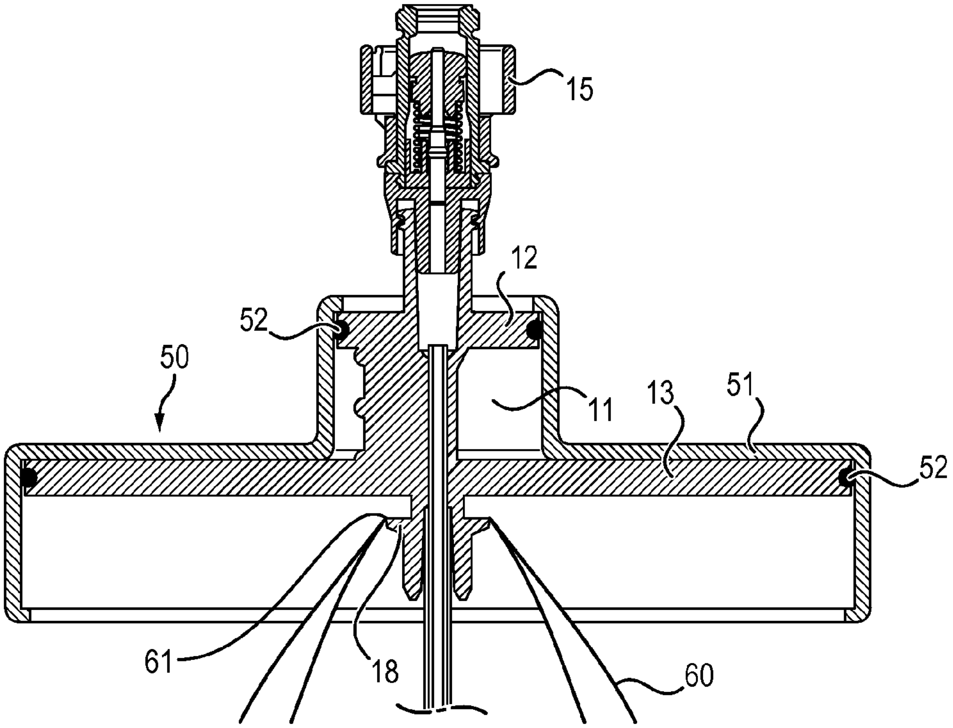
Figure 6B:
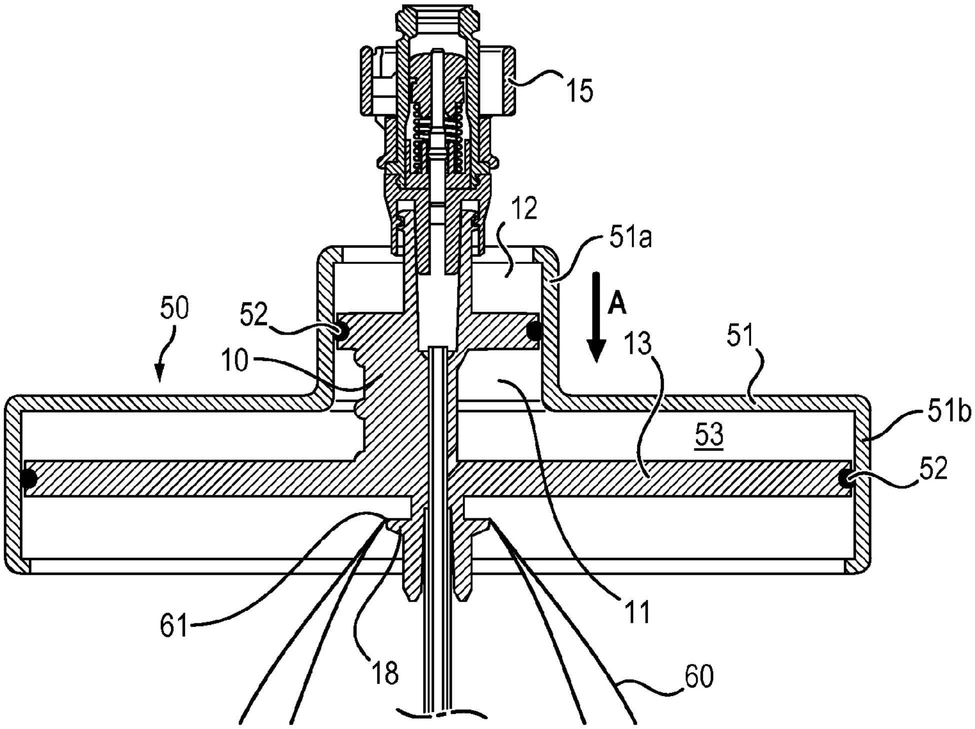
Figure 6C:
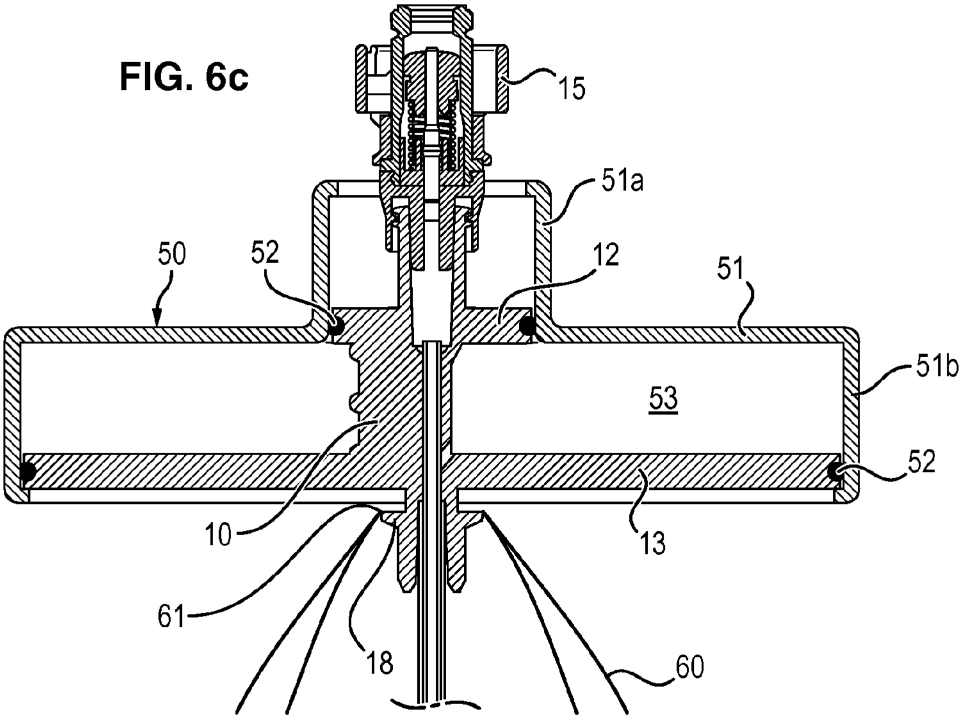
Figure 7:
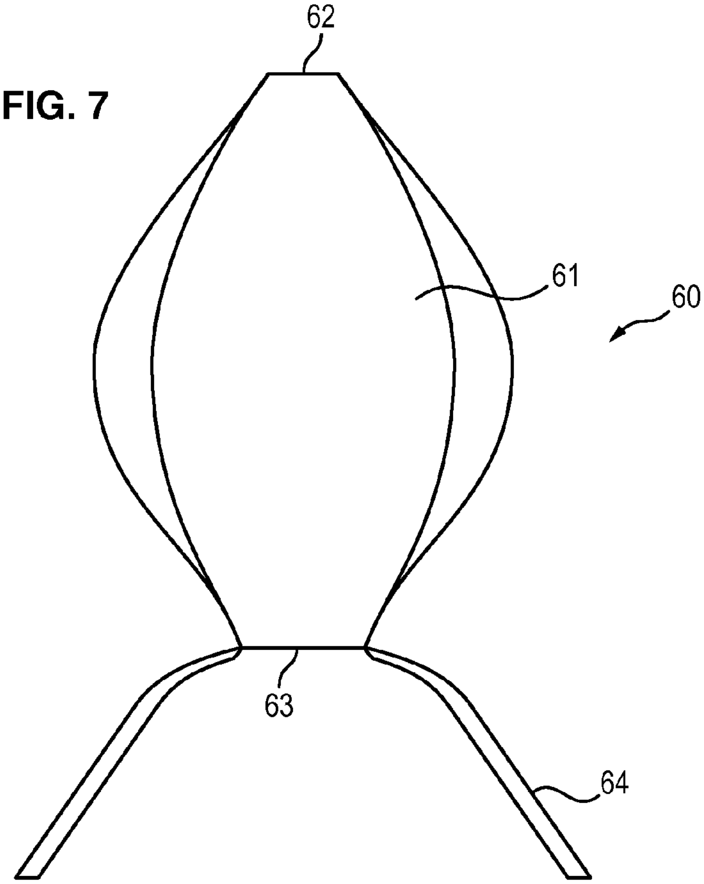
Figure 8:
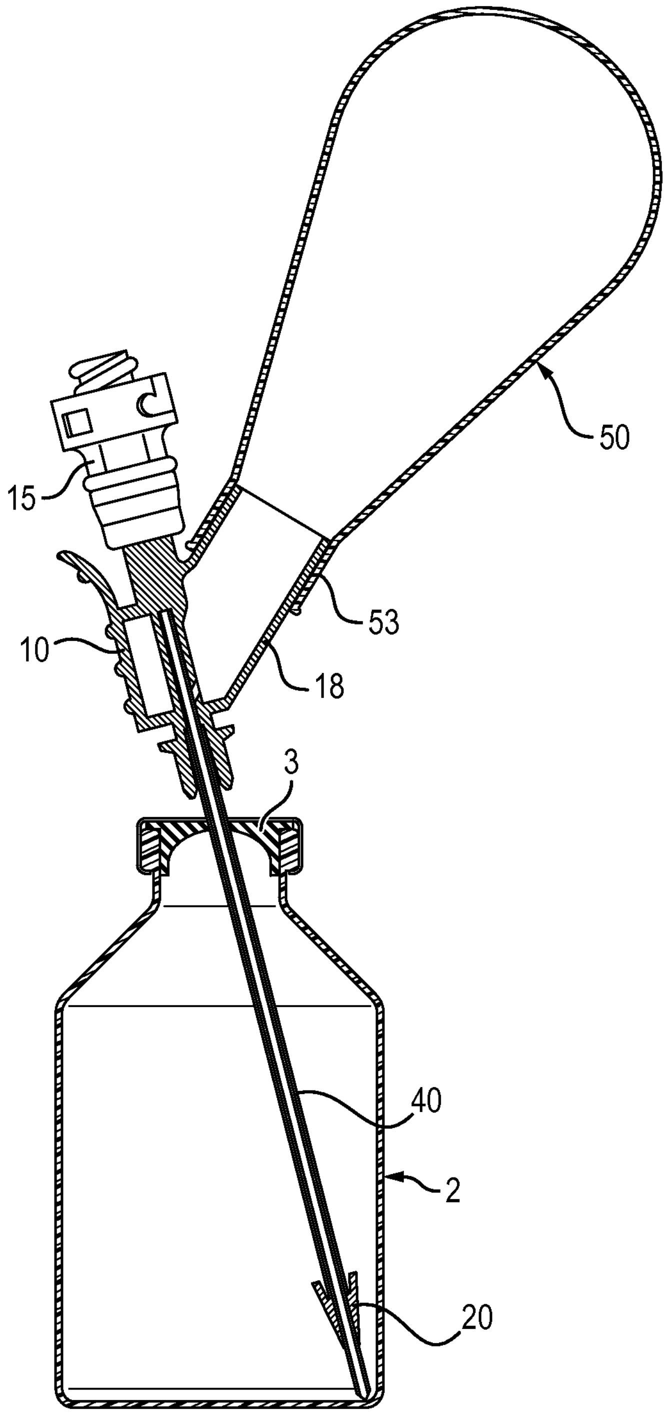

FIG. 4 is a cross-section view of an embodiment of a base of an interfacing device in accordance with the invention;

FIG. 5*a* is a partial cross-section view of the base of FIG. 4 whereon has been mounted a ball in accordance with an embodiment of the invention;

FIG. 5*b* is a partial cross-section view of another embodiment of the base whereon a ball has been mounted;

FIGS. 6*a* to 6*c* are cross-section views of an embodiment of the variable-volume reservoir of the interfacing device shown in FIG. 1*a*, at the various stages of its manipulation;

FIG. 7 shows an embodiment of a protective member of an interfacing device in accordance with the invention; and FIG. 8 is a cross-section view of the interfacing device of FIG. 2 in the process of manipulation.

An interfacing device in reference to the annexed figures shall now be described.

As shown in particular in the FIGS. 1*a*, 1*b* and 2, an interfacing device 1 in accordance with the invention is intended to be mounted on a puncturable flask 2 (or Vial) on its distal end 1*a*, and on a fluid injection instrument, such as a syringe (not shown in the figures), on its proximal end 1*b*.

The interfacing device 1 comprises in particular a base 10, of which a proximal end is provided with means for connecting 15 with the syringe, a means for puncturing 30 extending from the base 10 in the distal direction of the device 1, as well as a attachment means for attaching 20 the interfacing device 1 onto the Vial 2.

Any usual means of connecting in the field can be used. Preferably, means for connecting 15 will be selected that can limit the risks of the formation of drops and which can be cleaned easily, in that the drugs obtained risk to be harmful for the operator. Reference can be made in particular to the connectors described in patent application FR 1160164, filed on 8 Nov. 2011 in the name of the Applicant.

The base 10 comprises a body, which can for example come from moulding, comprising a generally cylindrical longitudinal chamber 14 opening at the distal end onto a duct 16. In FIG. 4 for example, the chamber 14 is of tapered revolution shape and the duct 16 is tubular.

According to the embodiments shown in the figures, a lateral orifice 11 opening into the duct 16 is made in the body of the base 10, whereon is fixed a variable-volume reservoir 50. Examples of such reservoirs 50 will be developed further on in the description.

The means for puncturing 30, here a needle, extends longitudinally from a distal end of the chamber 14 through the duct 16. The needle 30 is more preferably fixed in relation to the base 10, and extends where applicable facing the lateral orifice 11 of the base 10. Preferably, the needle 30 has on its distal end a tip 31, which can where applicable be bevelled.

Moreover, on duct 16, the base 10 further comprises a cannula 40, fixed in a sealed manner onto the base 10, more preferably at a distance (along a main extension axis X of the interfacing device 1) from the lateral orifice 11 in such a way as to leave a space between the distal end of the chamber 14 and the proximal end of the cannula 40.

Finally, the interfacing device 1 comprises on a distal end 1*a* a attachment means for attaching 20 the base 10 onto the Vial 2.

The attachment means for attaching 20 can be fixed between the distal end of the cannula 40 and the tip 31 of the needle 30, for example by over-moulding, gluing, welding, etc. on the needle 30, in such a way as to guarantee good mechanical adherence with the needle 30. In order to further improve the adherence of the attachment means for attaching 20 on the needle 30, the external surface of the needle 30 can be treated in the hooking zone of the attachment means for attaching 20 in such a way as to increase the friction between the two parts, for example by sanding said zone.

The attachment means for attaching 20 has a divergent proximal end 21 forming a shoulder and a convergent distal end 22 suitable for facilitating its penetration into the membrane 3 of the Vial 2. For example, the attachment means for attaching 20 can include a body 23 having a tapered revolution shape, of which the distal portion 22 is of a diameter substantially equal to the outer diameter of the needle 30, and of which the proximal portion 21 has a diameter substantially larger, typically twice as large.

In this way, the attachment means for attaching 20 can easily be inserted through the membrane 3 of the Vial 2, thanks to the tapered shape of the attachment means for attaching 20, then remain blocked inside the Vial 2, in that the proximal portion 21 of the attachment means for attaching 20 forms a shoulder which presses against an internal surface of the membrane 3 of the Vial 2 and prevents it from exiting, even in the case of a possible traction on the needle.

In the embodiment shown in particular in the FIGS. 3*a* and 3*b*, the attachment means for attaching 20 has the form of a harpoon, and comprises, in addition to the tapered revolution body 23, at least two lugs 21*a* that extend in the proximal direction in such a way as to reinforce the shoulder formed by the proximal portion 21 of the attachment means for attaching. A traction on the needle 30 anchors indeed the lugs 21*a* of the attachment means for attaching 20 in the membrane 3 of the Vial 2, as such reinforcing the resistance to the pulling off of the attachment means for attaching 20.

The number of lugs 21*a* is not of course limited, and can be equal to three, four or more. However, a limited number of lugs 21*a* shall be privileged, of a magnitude of two to four, in such a way as to prevent the risks of deterioration of the membrane 3. Preferably, the lugs 21*a* are then distributed angularly in such a way that the attachment means for attaching 20 are symmetrical.

According to a preferred embodiment, and as can be seen more particularly in FIGS. 3*a* and 4, the attachment means for attaching 20 make it possible to place in fluidic communication the puncturable flask 2 with a space external 4 to the interfacing device 1. For this, an inner diameter of the cannula 40 is greater than an outer diameter of the needle 30, in such a way as to create an annular channel 35 between the needle 30 and the cannula 40. Given the configuration of the cannula 40 and of the needle 30 on the base 10, the annular channel 35 therefore opens at the proximal portion in the duct 16 in such a way as to be in fluidic communication with the lateral orifice 11 of the base 10. Moreover, the annular channel 35 opens on its distal end at the exterior of the interfacing device 1, in such a way that the variable-volume reservoir 50 can be in fluidic communication with the external environment by attachment means for attaching 20 by the intermediary of the annular channel 35 and of the lateral orifice 11. As such, once the attachment means for attaching inserted into the Vial, the variable-volume reservoir is then in fluidic communication with inside of the Vial via the annular channel 35 and the lateral orifice 11.

For this, the attachment means for attaching 20 can include at least one indentation 24 extending transversally to the needle 30, and opening onto the distal portion of the annular channel 35. For example, in the embodiment shown in the annexed figures, the attachment means for attaching 20 can include at least one indentation 24 between each lug 21*a*.

Advantageously, the arrangement of the indentations 24 in the attachment means for attaching 20 in relation to the distal end of the annular channel 35 is such that at any moment the annular channel 35 opens into the Vial 2, and this even in the case of traction sur the interfacing device by the operator. This is made possible here by the implementation of lugs 21*a* of the attachment means for attaching 20 which, in case of traction on the device 1, prevent the needle 30 from rising back up beyond the indentations, guaranteeing as well that the annular channel 35 opens at any moment into the Vial 2.

Alternatively, instead of the annular channel 35, the interfacing device 1 can also include a means for diverting (not shown in the figures) suited to put in fluidic communication the surrounding environment by attachment means for attaching 20 with the lateral orifice 11. Such a means for diverting can for example be a pipe extending along the cannula 40 between the lateral orifice 11 and the indentation or indentations 24.

The objective of the variable-volume reservoir 50 is to arrange a reserve of gas 51 coming from a closed system without contact with the exterior, in order to limit, and even cancel, the exchanges of gas between the Vial 2 and the exterior. For this, the maximum internal volume of the variable-volume reservoir 50 is at least equal to the internal volume of the Vial 2.

Preferably, the reservoir 50 initially contains a sterile gas, for example sterile air.

In use, the gas initially enclosed in the reservoir 50 can be removed by the indentation 24 before insertion into the Vial 2, in particular when the Vial 2 initially contains powder and a gas, or on the contrary only after insertion.

More precisely, in the case of a Vial 2 initially containing a product in the form of a powder, the operator more preferably removes the gas initially contained in the reservoir 50 before inserting the attachment means for attaching 20 into the Vial 2. In this way, when the syringe is connected to the means for connecting 15 of the interfacing device 1, and that the fluid that it contains is inserted into the Vial in order to solubilise the product in the form of a powder, the gas initially contained in the Vial is flushed via the indentations 24, the annular channel 35 and the lateral orifice 11 from the base 10 towards the reservoir 50. Then, in a second temps, when the fluid is drawn by the syringe with the product in the form of a powder and of liquid, the gas flushed in the reservoir 50 is drawn via vacuum into the Vial 2. The cycle of injecting and of drawing the fluid loaded with powder can then be repeated until its solubilisation or homogenisation is complete.

The system formed of the interfacing device 1, of the Vial 2 and of the syringe is therefore closed and makes it possible to prevent any risk of air escaping and aerosolisation towards the exterior surroundings thanks to the variable-volume reservoir 50. Moreover, in the case of a reservoir 50 partially filled with sterile gas, the system comprising the interfacing device 1 and the Vial 2 is sterile before puncturing of the membrane 3 of the Vial 2 and remains sterile after puncturing, since there is no gaseous exchanges with the exterior.

Alternatively, in the case of a Vial 2 containing initially a fluid product, the operator more preferably does not remove the gas initially contained in the variable-volume reservoir 50 before inserting the attachment means for attaching 20 into the Vial 2. Indeed, when the operator draws the fluid contained in the Vial with the syringe, the gas initially contained in the reservoir is drawn via the lateral orifice 11 from the base 10, the annular channel 35 and the indentations 24 in order to fill the Vial 2.

In order to facilitate the operations of injecting and of drawing the fluid loaded with powder, the gas must more preferably be able to flow easily from the Vial 2 to the reservoir 50 and vice-versa. This flow is simplified here thanks in particular to the absence of valves and filters, as the latter are no longer useful in that the device 1 of the invention is in a closed circuit. Indeed, the fluids used are often relatively viscous and therefore require substantial efforts on the part of the operator, in particular during drawing.

According to the embodiments shown in the FIGS. 1*b*, 5*a*, and 5*b*, the variable-volume reservoir 50 can be an elastomeric ball.

The ball 50 is more preferably fixed on a lateral channel 17 of the base 10 adjacent to the lateral orifice 11, or at least is in fluidic communication with the latter. For example, the ball 50 can be glued or fixed on the base 10 by means of a ligation of a sleeve 53 tightening the lateral channel 17.

The ball 50 can extend transversally to the main extension axis X of the interfacing device 1, as shown in FIG. 5*a*.

Alternatively, the ball 50 can be inclined in relation to this axis X in such a way as to bring closer its centre of gravity with said axis X (see FIGS. 1*b* and 5*b*). In this way, when the interfacing device 1 is fixed on the Vial 2, the unit is more balanced and more stable than when the ball extends transversally. Moreover, this configuration allows any drops drawn with the gas during the manipulations to flow and to return into the Vial 2 via gravity.

In order to further improve the stability of the unit, the ball 50 can also extend around the main extension axis X of the interfacing device 1.

Alternatively, as shown in the FIGS. 1*a* and 6*a* a 6*c*, the variable-volume reservoir 50 can also be carried out in the form of a rigid reservoir extending around the base 10, transversally to the main extension axis X of the interfacing device 1, and include two parts complementary and mobile in translation in relation to one another in such a way as to make it possible to modulate the internal volume located between said parts.

For example, the parts can be a rigid casing 51, having a generally cylindrical shape, and closed on its proximal and distal ends by plates 12, 13, extending from the base 10. In the embodiments shown in the figures, the plates 12 and 13 extend transversally to the X axis, and the casing 51 is mobile in translation in a direction parallel to said axis, between the two plates 12, 13.

The casing 51 is assembled in a sealed manner with the plates 12 and 13, for example by means of seals 52.

For example, the casing 51 comprises a proximal portion 51*a*, of cylindrical shape and complementary with the shape of the proximal plate 12, and a distal portion 51*b*, of cylindrical shape and complementary with the distal plate 13. In order to guarantee the seal of the contact between the proximal portion 51*a* and the distal portion 51*b* of the casing 51 with the proximal 12 and distal 13 plates, the reservoir 50 is furthermore provided with seals 52, arranged more preferably between the proximal portion 51*a* and the proximal plate 12 on the one hand, and between the distal portion 51*b* and the distal plate 13 on the other hand.

In the embodiments shown, the casing 51, the plates 12, 13 and the seals 52 are of cylindrical revolution. Moreover, the plates 12 and 13 are fixed in relation to the base 10, with only the casing 51 mobile in translation along the X axis, according to the required volume of the reservoir 50. The plates 12 and 13 can then be formed integrally with the base 10, over-mounted on the latter or added.

It is of course understood that the volume of air 53 imprisoned in the reservoir depends on the distance between the two plates 12 and 13 and on their respective surfaces.

In use, when the reservoir 50 is empty (FIG. 6*a*), the distal portion 51*b* of the casing 51 is abutted against the upper surface of the distal plate 13 and the proximal portion 51*a* is abutted against the proximal plate 12, in such a way that the internal volume 53 of the reservoir 50 is zero. Then, when the reservoir 50 is filled progressively (FIG. 6*b*), the casing 51 slides in the direction of the arrow A along plates 12 and 13, as such drawing the gas contained in the Vial 2. Finally, when all of the gas imprisoned in the Vial 2 has been flushed into the casing 51, the internal volume 53 of the casing 51 is maximal and its distal end is abutted against the distal plate 13.

Alternatively, the casing 51 can be fixed in relation to the base 10 while the plates 12 and 13 can be mobile along the X axis, or both the casing 51 and the plates 12, 13 can be mobile in translation.

Advantageously, such a reservoir 50 being rigid, it does not present the risk of being accidentally punctured during its storage or its manipulation by an operator. Moreover, the sliding of the casing 51 along plates 12 and 13 makes it possible to vary in a simple and stable manner the volume of the reservoir 50 without destabilising the interfacing device 1.

The Applicant has observed that, due to the quality of the membrane 3 of the Vial 2, it could occur that one or several drops of the fluid drawn or injected into the Vial flow along the cannula 40, despite the use of a attachment means for attaching in accordance with the invention, and this even more so when the cannula 40 itself is placed into contact with the fluid (which is possible during the use of the device 1, as shall be seen further on in the description).

In order to prevent the operator from being in contact with these possible drops, the interfacing device 1 can, optionally, further include a protective member 60 of the attachment means for attaching 20 and of the cannula 40. Such an protective member 60 can for example have the shape of an envelope 61 extending between a proximal ring 62 and a distal ring 63 diametrically opposite, the proximal ring 62 being suited to be fixed on the base 10 in such a way that the envelope 61 covers all or a portion of the distal portion 1*a* of the interfacing device 1, in order to limit the risks of contamination of the operator and of the contents of the Vial 2. Advantageously, the envelope 61 of the protective member 60 entirely covers the cannula 40 and the attachment means for attaching 40, in order to prevent any risk of contamination.

The proximal ring 62 and the distal ring 63 are suited to be fixed respectively onto the base 10 and a neck of the Vial 2 in such a way as to delimit an internal volume. Moreover, in order to facilitate the manipulation of the protective member 60, the latter can furthermore include a means for grasping 64, for example two grasping strips extending on either side of the distal ring 63.

For example, the proximal ring 62 of the protective member 60, which can for example be of circular or elliptical shape, can be fixed by gluing, welding, locking or by means of an elastic sleeve on a portion 18 of the base 10.

The distal ring 63 can be applied in force onto the neck of the Vial 2, more preferably with sealed tightening.

The distal ring 63 can for example be circular.

Alternatively, the distal ring 63 is of elliptical shape in order to improve the sealed tightening of the device 60 onto the neck of the Vial. The possible grasping strips 64 are then arranged more preferably on either side of its large axis, in such a way that a traction on the strips 64 in the direction of the neck of the Vial 2 increases the length of the small axis of the distal ring 63 and facilitates its press fitting onto the neck of the Vial 2.

In order to guarantee a strong hold in pressure of the distal ring 63 on the neck of the Vial, the dimensions of the large axis of the distal ring 63 (or, when the distal ring 63 is circular, its diameter) can be smaller than the diameter of the neck of the Vial 2.

Alternatively, at least one of the grasping strips 64 can have an adhesive surface protected where applicable by a peelable protective film (typically, a siliconised paper). Preferably, the surfaces facing the two grasping strips 64 are adhesive. In this way, in use, once the distal ring 63 is press fitted onto the neck of the Vial, the operator removes the peelable protective films and fixes the strips 64 onto the Vial 2 in order to maintain the protective member 60 in position on the flask 2.

A method for using an interfacing device 1 in accordance with the invention shall now be described, in the case of a flask containing a product in the form of a powder. Those skilled in the art will easily be able to adapt this method to a flask initially containing a fluid, with the sole difference residing in the fact that the reservoir 50 is not empty initially.

In a first step, the operator flushes the gas initially contained in the variable-volume reservoir 50. In the case of a ball 50, it is sufficient to press it until all of the gas is flushed from the latter, while in the case of the rigid reservoir 50 shown in particular in FIGS. 6*a* to 6*c*, the operator must slide the casing 51 along the base 10 until the latter arrives abutted against the plates 12 and 13.

The operator can then puncture the membrane 3 of the Vial 2 by pushing the tip 31 of the needle 30 through the membrane 3. In order to facilitate this puncturing, the Vial 2 can be placed vertically on a support, the neck upwards, and the tip 31 of the needle 30 can be inserted into the membrane 3 from top to bottom.

Optionally, when the interfacing device 1 comprises a protective member 60, which can be where applicable pre-fixed onto the base 10, the operator fixes the distal ring 63 of the protective member 60 onto the neck of the Vial 2, in order to prevent any contamination by the product that it contains.

In a second step, the operator connects the syringe to the means for connecting 15 the interfacing device 1, more preferably making sure to avoid any formation of drops in order to limit the risks of contamination, and injects a fluid into the Vial 2.

The injection of fluid into the Vial 2 has for effect to flush the gas initially present in the Vial 2 towards the reservoir 50, of which the internal volume then increases proportionately to the gas received. In the case of the rigid reservoir 50, the casing 51 slides for example until it abuts with the distal plate 13.

In a third step, the operator draws and then reinjects the fluid loaded with product several times, in such as way as to solubilise the product in the form of a powder in the fluid and to homogenise it.

This manipulation can in particular be facilitated by turning over the unit formed by the syringe, the Vial 2 and the interfacing device, in such a way that the Vial 2 is above the interfacing device 1 and that the fluid that it contains flows by gravity towards its neck. This position is indeed more ergonomic for the operator and less tiresome, in particular when the fluid is viscous. Moreover, thanks to the use (optional) of the protective member 60, the operator is protected from any drops that could slide along the cannula 40 during the manipulation, in the case of a membrane 3 of poor quality or deteriorated, or of an incorrect manipulation of the device 1.

In case the unit is turned over, for the injection of fluid into the Vial 2, the attachment means for attaching 20 is more preferably driven into the Vial 2 in such a way that the indentation 24 and the distal portion of the annular channel 35 are above the level of the fluid, i.e. in the space of the Vial that contains the gas, in such a way as to prevent fluid from penetrating into the annular channel 35 and flows into the reservoir 50. Otherwise, it would indeed be necessary for the operator to provide more substantial effort in order to inject the liquid into the Vial 2, without counting that this increase in pressure furthermore risks facilitating the passage of the fluid into the annular channel 35.

For the drawing of the fluid by the syringe, the operator must ensure on the contrary that the tip 31 of the needle 30 is immersed in the fluid in order to prevent drawing the gas with the syringe. If however gas were to be drawn, the operator could nevertheless empty the air from the syringe conventionally more preferably making sure to reinject it into the Vial 2 in order to prevent any risk of contamination by the product.

As the fluid is drawn by the syringe, the level of fluid decreases in the Vial 2 until it reaches the tip 31 of the needle 30. It is then possible to pull on the needle 30, in such a way as to lower the tip 31 and maintain it under the level of the fluid. Then, when the latter is no longer possible due to the presence of the attachment means for attaching which prevents the tip 31 of the needle 30 from exiting beyond a certain point from the Vial, the operator can then turn over the unit formed by the Vial 2, the interfacing device 1 and the syringe, and push the needle 30 towards the bottom of the Vial in such a way as to be able to reach the remainder of the fluid.

In order to facilitate the drawing of the fluid, the operator can in particular pivot the needle 31 in the Vial 2, as shown in FIG. 8. The connection between the cannula 40 and the membrane 3 is indeed of the ball and socket type through the flexibility of the membrane 3 and the shape of the cannula 40, and therefore allows the operator to access all of the internal volume of the Vial 2. It will therefore be understood that the utility of the protective member 60 (optional) in the case where the operator effectively drives the cannula 40 to the bottom of the Vial 2, since the latter comes into contact with the product contained by the Vial 2 and can remain on the cannula 40 when the operator extracts it from the Vial 2.

Of course, this invention is in no way limited to the embodiments described hereinabove and shown in the drawings, but those skilled in the art will know how to add numerous variants and modifications.

The invention claimed is:

1. Interfacing device intended to connect a fluid injection instrument and a puncturable flask, comprising:

a base suitable for connecting the interfacing device to the fluid injection instrument, an attachment means for attaching the base to the puncturable flask, arranged at a distal end of the interfacing device, having a divergent proximal end forming a shoulder and a convergent distal end suitable for facilitating a penetration of the attachment means for attaching into the puncturable flask, wherein the attachment means for attaching comprises at least one indentation in a zone adjacent to its proximal end, suited to place in fluidic communication the puncturable flask with a variable-volume reservoir fixed in a sealed manner to the base, a means for puncturing the puncturable flask, and a cannula threaded onto the means for puncturing between the base and the attachment means for attaching.

2. Interfacing device according to claim 1, wherein the means for puncturing is a needle of which the distal end is in the form of a tip.

3. Interfacing device according to claim 1, wherein the attachment means for attaching is fixed on a distal end of the means for puncturing.

4. Interfacing device according to claim 1, wherein the attachment means for attaching is over-moulded in a zone adjacent to the distal end of the means for puncturing.

5. Interfacing device according to claim 1, wherein an inner diameter of the cannula is greater than an outside diameter of the means for puncturing in such a way as to form an annular channel between the cannula and the means for puncturing.

6. Interfacing device according to claim 5, wherein the indentation is suited to place in fluidic communication the annular channel with the space external to the interfacing device.

7. Interfacing device according to claim 6, further comprising the variable-volume reservoir fixed in a sealed manner onto the base and in fluidic communication with the annular channel.

8. Interfacing device according to claim 7, having a main extension axis, wherein the variable-volume reservoir is an elastomeric or thermoplastic ball, and wherein the ball extends transversally in relation to said main extension axis.

9. Interfacing device according to claim 1, having a main extension axis, and wherein the variable-volume reservoir extends transversally to said main extension axis of the interfacing device entirely or partially around the base, and comprises a support and a casing assembled together in a sealed manner and mobile in translation in relation to one another.

10. Interfacing device according to claim 1, wherein the support is formed of a proximal plate and of a distal plate substantially parallel and integral in translation, and wherein the casing and the support are able to be displaced in relation to one another in a direction perpendicular to said plates.

11. Interfacing device according to claim 1, wherein the cannula is fixed in relation to the means for puncturing.

12. Interfacing device according to claim 1, wherein the cannula is abutted against the attachment means for attaching.

13. Interfacing device intended to connect a fluid injection instrument and a puncturable flask, comprising:

a base suitable for connecting the interfacing device to the fluid injection instrument, an attachment means for attaching the base to the puncturable flask, arranged at a distal end of the interfacing device, having a divergent proximal end forming a shoulder and a convergent distal end suitable for facilitating a penetration of the attachment means for attaching into the puncturable flask, and a protective member fixed on the base and covering entirely or partially the attachment means for attaching, wherein the protective member is an envelope extending between a proximal end and a distal end diametrically opposite, the proximal end being suited to be fixed onto the base in such a way that the envelope covers at least partially a distal portion of the interfacing device in order to limit the risks of contamination.

* * * * *